United States Patent

Marschner et al.

Patent Number: 5,488,127
Date of Patent: Jan. 30, 1996

[54] AMINOPHENOLS USEFUL AS INTERMEDIATES FOR FORMAZAN REACTIVE DYES

[75] Inventors: Claus Marschner, Speyer; Manfred Patsch, Wachenheim, both of Germany

[73] Assignee: BASF Aktiengesellschaft, Ludwigshafen, Germany

[21] Appl. No.: 407,956

[22] Filed: Mar. 22, 1995

Related U.S. Application Data

[62] Division of Ser. No. 136,131, Oct. 15, 1993, Pat. No. 5,446,193.

[30] Foreign Application Priority Data

Oct. 16, 1992 [DE] Germany ............ 42 34 900.1

[51] Int. Cl.$^6$ ................................................ C07C 317/28
[52] U.S. Cl. .................... 558/25; 558/30; 562/47; 564/50; 544/390
[58] Field of Search ............... 534/618; 558/25, 558/30; 562/47; 564/50

[56] References Cited

U.S. PATENT DOCUMENTS

| | | | |
|---|---|---|---|
| 4,841,028 | 6/1989 | Aeschlimann et al. | 534/618 X |
| 5,214,207 | 5/1993 | Siegel et al. | 564/50 |
| 5,354,882 | 10/1994 | Siegel et al. | 558/30 |
| 5,380,941 | 1/1995 | Siegel et al. | 564/50 X |

*Primary Examiner*—Johann Richter
*Assistant Examiner*—Fiona T. Powers
*Attorney, Agent, or Firm*—Oblon, Spivak, McClelland, Maier & Neustadt

[57] ABSTRACT

There are described formazan dyes of the formula

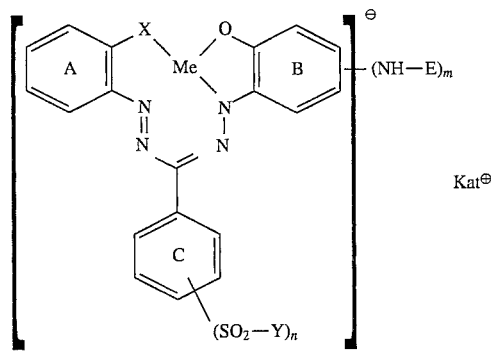

where
m and n are each 1 or 2,
Kat$^\oplus$ is the equivalent of a cation,
Me is copper or nickel,
X is oxygen or a radical of the formula CO—O or SO$_2$—O,
Y is vinyl or a radical of the formula C$_2$H$_4$—Q, wherein Q is a group that is detachable under alkaline reaction conditions,
E is a fiber-reactive radical,
the rings A and B may be substituted and benzofused, and
the ring C may be substituted,
the use thereof for dyeing or printing hydroxyl- or nitrogen-containing organic substrates, novel aminophenols and a process for preparing same.

1 Claim, No Drawings

AMINOPHENOLS USEFUL AS INTERMEDIATES FOR FORMAZAN REACTIVE DYES

This is continuation, of application Ser. No. 08/136,131 filed on Oct. 15, 1993, now U.S. Pat. No. 5,446,193.

The present invention relates to novel formazan dyes of the formula I

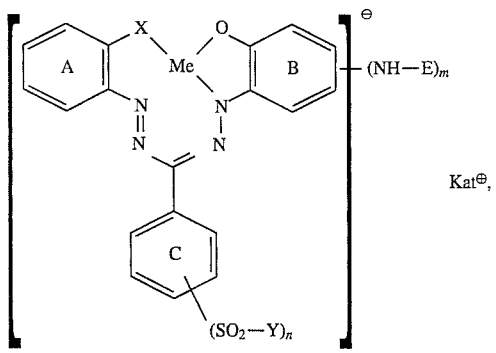

where m and n are each independently of one another 1 or 2, $Kat^\oplus$ is the equivalent of a cation, Me is copper or nickel, X is oxygen or a radical of the formula CO—O or $SO_2$—O, Y is vinyl or a radical of the formula $C_2H_4$—Q, wherein Q is a group that is detachable under alkaline reaction conditions, E is a heterocyclic fiber-reactive radical or a fiber-reactive radical of the formula L—W, wherein L is a bridge member and W is a fiber-reactive radical of the aliphatic series, the rings A and B are each substituted or unsubstituted and may be benzofused, and the ring C is substituted or unsubstituted, the use thereof for dyeing or printing hydroxyl- or nitrogen-containing organic substrates, novel aminophenols, and a process for preparing them.

Metal complex formazan dyes with reactive groups are known per se; see for example EP-A-28 788. However, the prior art dyes frequently have defects in their application properties.

It is an object of the present invention to provide novel formazan-based reactive dyes which shall be notable for an advantageous application property profile.

We have found that this object is achieved by the formazan dyes of the formula I defined at the beginning.

Attention must be drawn in particular to formazan dyes of the formula Ia

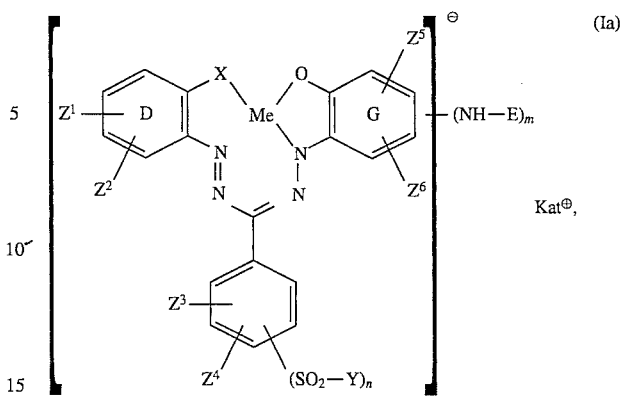

where $Z^1$ is hydrogen or hydroxysulfonyl, $Z^2$ is hydrogen, $C_1$–$C_4$-alkanoylamino, halogen or nitro, $Z^3$ and $Z^4$ are each independently of one another hydrogen, halogen, $C_1$–$C_4$-alkyl, $C_1$–$C_4$-alkoxy, $C_1$–$C_4$-alkylsulfonyl, nitro or hydroxysulfonyl, $Z^5$ and $Z^6$ are each independently of one another hydrogen, hydroxysulfonyl, halogen, nitro, carboxyl, ureido, substituted or unsubstituted mono- or di($C_1$–$C_4$-alkyl)ureido, substituted or unsubstituted phenylureido, substituted or unsubstituted phenyl, substituted or unsubstituted $C_1$–$C_4$-alkanoylamino, substituted or unsubstituted benzoylamino, $C_1$–$C_4$-alkoxycarbonylamino, substituted or unsubstituted mono- or dialkylcarbamoyl or substituted or unsubstituted mono- or dialkylsulfamoyl, the rings D and G may each be benzofused, and m, n, $Kat^\oplus$, Me, E, X and Y are each as defined above.

Any alkyl appearing in the abovementioned formulae may be straight-chain or branched.

Any substituted alkyl appearing in the abovementioned formulae may have as substituents for example, unless otherwise stated, hydroxysulfonyl, carboxyl, hydroxyl or sulfato. The number of substituents in substituted alkyl is in general 1 or 2.

Any substituted phenyl appearing in the abovementioned formulae may have as substituents for example, unless otherwise stated, $C_1$–$C_4$-alkyl, $C_1$–$C_4$-alkoxy, halogen, nitro, $C_1$–$C_4$-alkanoyl, $C_1$–$C_4$-alkanoylamino, benzoylamino or hydroxysulfonyl. The number of substituents in substituted phenyl is in general from 1 to 3.

$Kat^\oplus$ is the equivalent of a cation. It constitutes either a proton or is derived from metal or ammonium ions. Metal ions are in particular lithium, sodium and potassium ions. Ammonium ions for the purposes of the present invention are substituted or unsubstituted ammonium cations. Substituted ammonium cations are for example monoalkyl-, dialkyl-, trialkyl-, tetralkyl- or benzyltrialkyl-ammonium cations or cations derived from nitrogen-containing five- or six-membered saturated heterocycles, such as pyrrolidinium, piperidinium, morpholinium, piperaziniumor N-alkylpiperaziniumcations or their N-monoalkyl- or N,N-dialkyl-substituted products. Alkyl used herein in the general sense of meaning straight-chain or branched $C_1$–$C_{20}$-alkyl which may be substituted by hydroxyl and/or interrupted by oxygen atoms in ether function.

Particularly notable cations are protons and lithium, sodium and potassium ions.

Q is a group that is detachable under alkaline reaction conditions. Examples of groups of that kind are chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, substituted or unsubstituted phenylsulfonyloxy, $C_1$–$C_4$-alkanoyloxy, $C_1$–$C_4$-dialkylamino and a radical of the formula

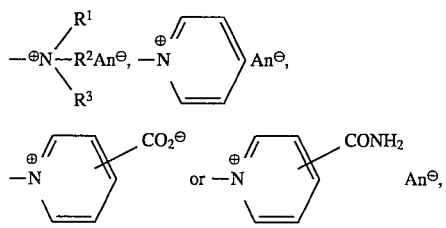

where $R^1$, $R^2$ and $R^3$ are identical or different and each is independently of the others $C_1$–$C_4$-alkyl or benzyl and is in each case the equivalent of an anion. Suitable anions are for example fluoride, chloride, bromide, iodide, mono-, di- or trichloroacetate, methanesulfonate, benzenesulfonate and 2- or 4-methylbenzenesulfonate.

$Z^2$, $Z^3$, $Z^4$, $Z^5$ and $Z^6$ are each for example fluorine, chlorine or bromine.

$Z^5$ and $Z^6$ may each also be for example N-methylureido, N-ethylureido, N-propylureido, N-isopropylureido, N-butylureido, N-(2-hydroxysulfonylethyl)ureido, N-(2-sulfatoethyl)ureido, N,N-dimethylureido, N-methyl-N-(2-sulfatoethyl)ureido, phenylureido, phenyl, 2-, 3- or 4-methylphenyl, 2-, 3- or 4-methoxyphenyl, 2-, 3- or 4-chlorophenyl, 2-, 3- or 4-hydroxysulfonylphenyl, formylamino, acetylamino, propionylamino, butyrylamino, isobutyrylamino, 3-hydroxysulfonylpropionylamino, 3-carboxypropionylamino, benzoylamino, 2-, 3- or 4-hydroxysulfonylbenzoylamino, 2-, 3- or 4-chlorobenzoylamino, 2-, 3- or 4-methylbenzoylamino, 2-, 3- or 4-carboxybenzoylamino, methoxycarbonylamino, ethoxycarbonylamino, propoxycarbonylamino, isopropoxycarbonylamino, butoxycarbonylamino, carbamoyl, mono- or dimethylcarbamoyl, mono- or diethylcarbamoyl, mono- or dipropylcarbamoyl, mono- or diisopropylcarbamoyl, mono- or dibutylcarbamoyl, N-methyl-Nethylcarbamoyl, N-methyl-N-(2-hydroxysulfonylethyl)carbamoyl, sulfamoyl, mono- or dimethylsulfamoyl, monoor diethylsulfamoyl, mono- or dipropylsulfamoyl, mono- or diisopropylsulfamoyl, mono- or dibutylsulfamoyl, N-methyl-N-ethylsulfamoyl or N-methyl-N-(2-hydroxysulfonylethyl)sulfamoyl.

$Z^2$ may also be for example formylamino, acetylamino, propionylamino, butyrylamino or isobutyrylamino.

$Z^3$ and $Z^4$ may each also be for example methyl, ethyl, propyl, isopropyl, butyl, isobutyl, sec-butyl, methoxy, ethoxy, propoxy, isopropoxy, butoxy, isobutoxy, sec-butoxy, methylsulfonyl, ethylsulfonyl, propylsulfonyl, isopropylsulfonyl or butylsulfonyl.

Fiber-reactive radicals E are those which react substitutively or additively with the hydroxyl or nitrogen groups of the substrates to be treated.

Substitutively means, for example in the case of the reaction of the fiber-reactive radical with the hydroxyl groups of cellulose, that the leaving group or atoms (eg. fluorine or chlorine) in the fiber-reactive radical E are replaced by the hydroxyl groups of cellulose in accordance with the following scheme:

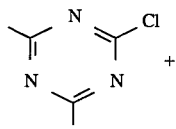
+

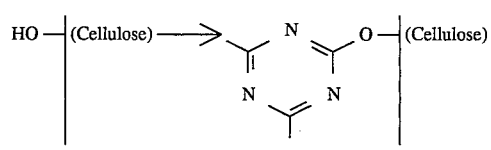

Additively means, for example in the case of a reaction of the fiber-reactive radical with the hydroxyl groups of cellulose, that the hydroxyl groups of cellulose add to the fiber-reactive radical in accordance with the following scheme:

$-SO_2-CH=CH_2 +$

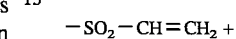

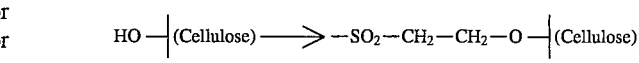

Heterocyclic fiber-reactive radicals E are for example halogen-substituted radicals of 1,3,5-triazine, quinoxaline, phthalazine, pyrimidine or pyridazone, or the 2-alkylsulfonylbenzothiazole radical.

Examples are the following heterocyclic radicals:

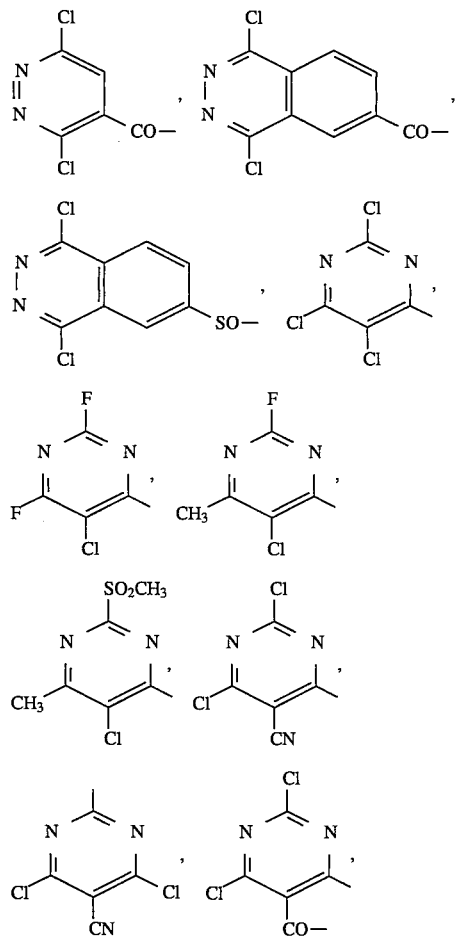

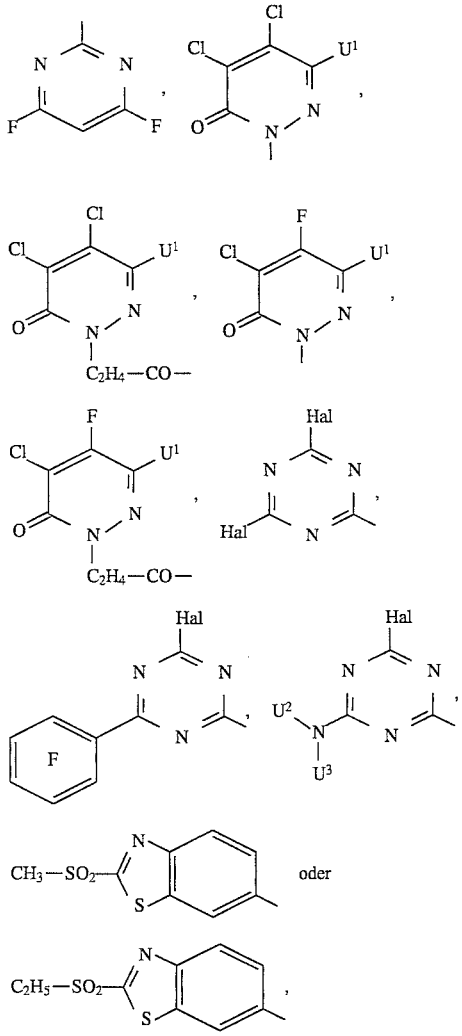

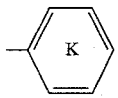

wherein

Hal is fluorine or chlorine, $U^1$ is hydrogen or nitro, and $U^2$ and $U^3$ singly are independently of each other hydrogen or $C_1$–$C_6$-alkyl, which may be substituted by hydroxyl, halogen, cyano, hydroxysulfonyl or a radical of the formula —$SO_2$—Y, wherein Y is as defined above, and may be interrupted by 1 or 2 oxygen atoms in ether function, by imino or by $C_1$–$C_4$-alkylimino groups, or together with the nitrogen atom joining them together pyrrolidinyl, piperidinyl, morpholinyl, piperazinyl or N-($C_1$–$C_4$-alkyl)piperazinyl, or else $U^2$ is a radical of the formula where the rings F and K may each be monosubstituted or disubstituted by hydroxysulfonyl and benzofused and the ring K may independently thereof be monosubstituted or disubstituted by chlorine, nitro, $C_1$–$C_4$-alkyl, $C_1$–$C_4$-alkoxy, cyano, carboxyl, acetylalnino, hydroxysulfonylmethyl methyl or a radical of the formula $CH_2$—$SO_2$—Y, $SO_2$—Y, NH—CO—Y or $NU^2$—CO—$NU^2$—$L^1$—$SO_2$—Y wherein Y and $U^2$ are each as defined above and $L^1$ is $C_2$–$C_6$-alkylene, which may be substituted by hydroxyl, chlorine, cyano, carboxyl, $C_1$–$C_4$-alkoxycarbonyl, $C_1$–$C_4$-alkanoyloxy or sulfato and may be interrupted by 1 or 2 oxygen atoms in ether function or by imino or $C_1$–$C_4$-alkylimino groups.

Fiber-reactive radicals W of the aliphatic series are for example acryloyl, mono-, di- or trichloroacryloyl, —CO—CCl═CH—COOH, —CO—CH═CCl—COOH, 2-chloropropionyl, 3-phenylsulfonylpropionyl, 3-methylsulfonylpropionyl, 2-sulfatoethylaminosulfonyl, 2-fluoro-2-chloro-3,3-di-fluorocyclobut-1-yl-carbonyl, 2,2,3,3-tetrafluorocyclobut-1-yl-carbonyl, 2,2,3,3-tetrafluorocyclobut-1-ylsulfonyl, 2-(2,2,3,3-tetrafluorocyclobut-1-yl) acryloyl, 1- or 2-bromoacryloyl, 1- or 2-alkyl- or -aryl-sulfonylacryloyl, such as 1- or 2-methylsulfonylacryloyl, 1,2-dichloropropionyl, 1,2-dibromopropionyl or a radical of the formula $SO_2$—Y where Y is as defined above.

Suitable bridge members L which link the aliphatic fiber-reactive radical W to the amino group of the formazan conform for example to the formula

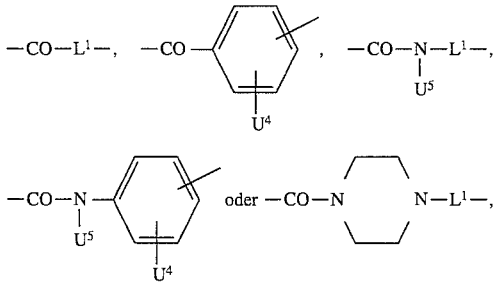

where $U^4$ is hydrogen, $C_1$–$C_4$-alkyl, carboxyl, $C_1$–$C_4$-alkoxy, halogen, nitro or hydroxysulfonyl, is hydrogen, $C_1$–$C_6$-alkyl, which may be substituted by hydroxyl, $C_1$–$C_4$-alkoxy, halogen, cyano, hydroxysulfonyl or a radical of the formula —$SO_2$—Y, where Y is as defined above, or is substituted or unsubstituted phenyl, and $L^1$ is as defined above.

The fiber-reactive radical E may also comprise a further formazan radical which is either identical to the formazan radical already present or different therefrom.

Of particular suitability in this case are copper formazan dyes of the formula V

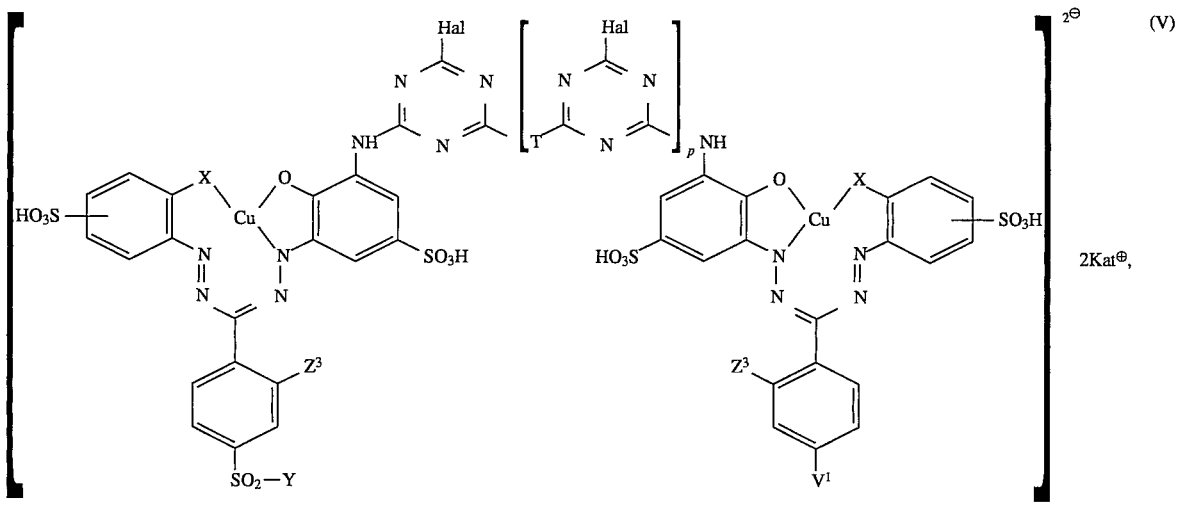

where
p is 0 or 1,
T is a radical of the formula

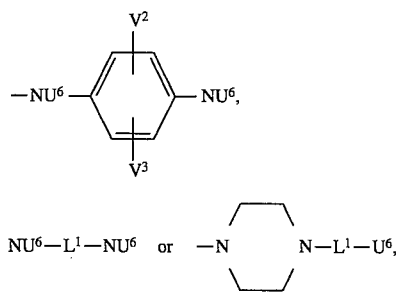

where
$U^6$ is hydrogen or $C_1$–$C_4$-alkyl and $V^2$ and $V^3$ are each independently of the other hydrogen or hydroxysulfonyl, and $L^1$ is in each case as defined above, and
$V^1$ is hydrogen or the radical $SO_2$—Y, and
Hal, X, Y, $Z^3$ and $Kat^\oplus$ are each as defined above.

Preference is given to formazan dyes of the formula I where Me is copper.

Preference is further given to formazan dyes of the formula I where m and n are each 1.

Preference is further given to formazan dyes of the formula I where Y is vinyl or a radical of the formula $C_2H_4$—Q where Q is chlorine, sulfato or thiosulfato, in which chlorine is mentioned in particular.

Preference is further given to formazan dyes of the formula I where X is a radical of the formula CO—O.

Particular preference is given to formazan dyes conforming to the formula Ib

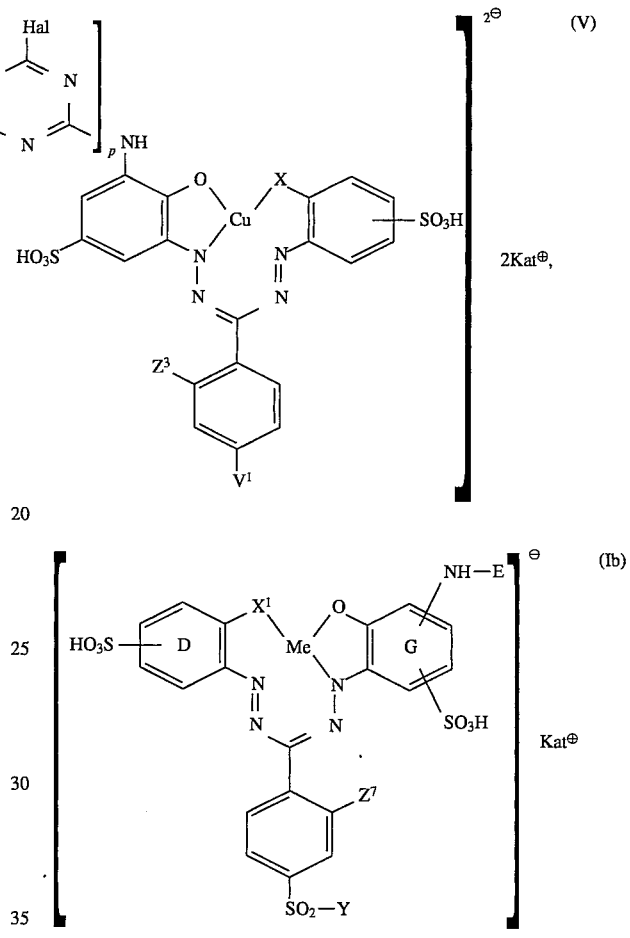

where
$Z^7$ is hydrogen, $C_1$–$C_4$-alkyl, hydroxysulfonyl or halogen,
$X^1$ is a radical of the formula CO—O or $SO_2$—O, and
Me, Y, E, $Kat^\oplus$ and the rings D and G are each as defined above.

Attention may be drawn in particular to formazan dyes of the formula Ic

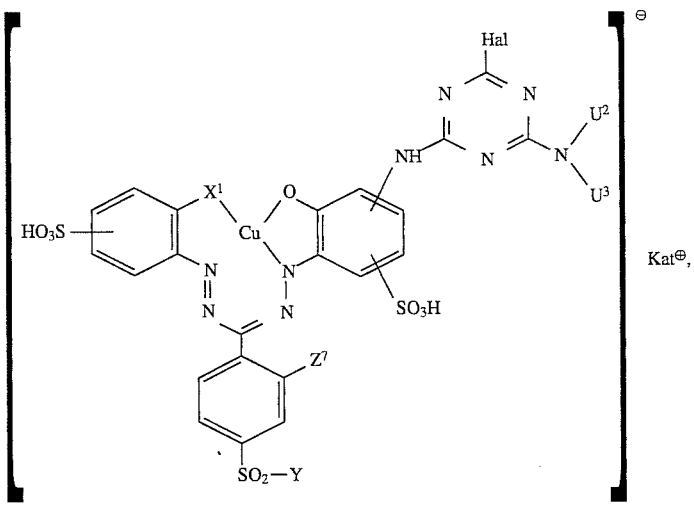

where
$U^2$, $U^3$, Hal, $X^1$, Y, $Z^7$ and $Kat^\oplus$ are each as defined above.

Attention may further be drawn to formazan dyes of the formula Id

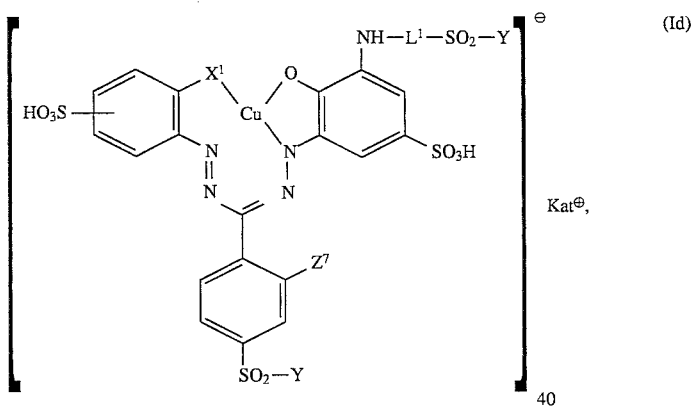

where $L^1$, $X^1$, Y, $Z^7$ and $Kat^\oplus$ are each as defined above.

of particular interest are formazan dyes of the formula Ie

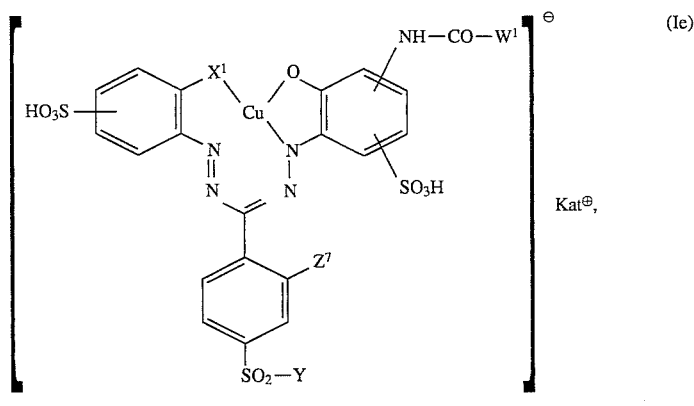

where
$W^1$ is a radical of the formula $alk^1$—$SO_2$—Y or where $alk^1$ is $C_3$–$C_5$-alkylene, and $X^1$, Y, $Z^7$ and $Kat^\oplus$ are each as defined above.

Also of particular interest are formazan dyes of the formula If

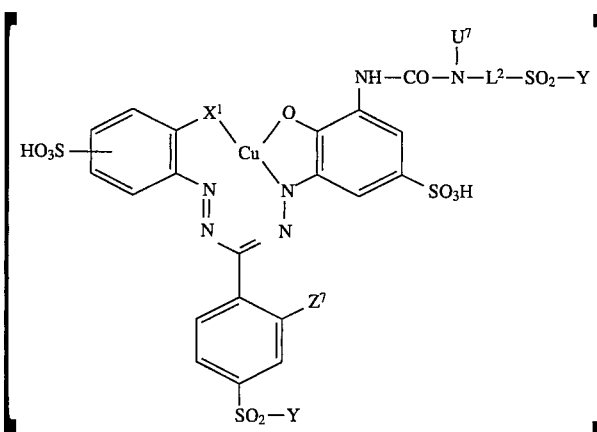
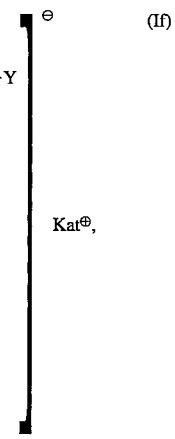

where

U⁷ is hydrogen or $C_1$–$C_4$-alkyl, which may be substituted by a radical of the formula $SO_2$-Y and may be interrupted by an oxygen atom in ether function, L² is a radical of the formula

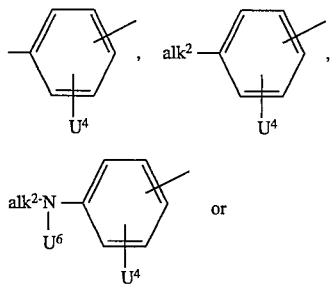

-alk²- wherein U⁴ and U₆ are each as defined above and alk² is in each case $C_2$–C4-alkylene, which may be interrupted by an oxygen atom in ether function, and X¹, Y, Z⁷ and Kat⊕ are each as defined above.

The present invention further relates to aminophenols of the formula II

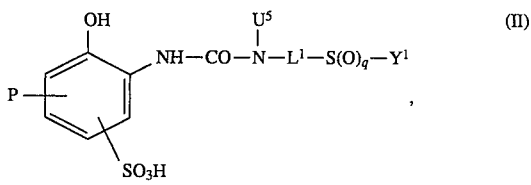

where q is 0 or 2,

Y¹ is vinyl or a radical of the formula $C_2H_4$—Q¹, wherein Q¹ is a group that is detachable under alkaline reaction conditions or hydroxyl, L is $C_2$–$C_6$-alkylene, which may be substituted by hydroxyl, chlorine, cyano, carboxyl, $C_1$–$C_4$-alkoxycarbonyl, $C_1$–$C_4$-alkanoyloxy or sulfato and may be interrupted by 1 or 2 oxygen atoms in ether function or by imino or $C_1$–$C_4$-alkylimino groups, U⁵ is hydrogen or $C_1$–$C_6$-alkyl, which may be substituted by hydroxyl, $C_1$–$C_4$-alkoxy, halogen, cyano, hydroxysulfonyl or a radical of the formula —$SO_2$—Y¹, wherein Y¹ is as defined above, or is substituted or unsubstituted phenyl, and P is nitro or amino.

Preference is given to aminophenols of the formula IIa

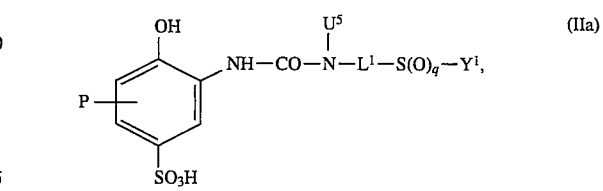

where q, Y¹, L¹, U⁵ and P are each as defined above.

Especial mention must be given to aminophenols of the formula II where L¹ is $C_2$–$C_4$-alkylene, which may be interrupted by one oxygen atom in ether function.

Especial mention must further be given to aminophenols of the formula II where U⁵ is hydrogen or $C_1$–$C_4$-alkyl, which may be substituted by a radical of the formula $SO_2$=—Y¹ and may be interrupted by an oxygen atom in ether function.

The novel aminophenols of the formula II are useful intermediates for preparing the formazan dyes of the formula I.

We have further found that the aminophenols of the formula II are obtainable in an advantageous manner by reacting a benzoxazolone of the formula III

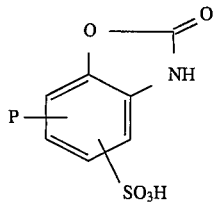

where P is as defined above, with an amine of the formula IV

where q, U⁵, L¹ and Y¹ are each as defined above.

The process of the invention is advantageously carried out in water or in a polar organic solvent, for example in a $C_1$–$C_4$-alkanol or in N,N-dimethylformamide, at from 50° to 95° C. and at a pH of from 5 to 9, preferably from 6 to 7.5.

Thereafter conventional methods can be employed, if necessary, to oxidize the thioether to a sulfone group, to reduce the nitro to an amino group, and to introduce the alkali-detachable group Q.

The benzoxazolones of the formula III can be obtained in a conventional manner, for example by reaction of the corresponding o-aminophenols with phosgene, as more particularly described in the Examples.

In a preferred embodiment of the process according to the present invention, the benzoxazolones formed in the reaction of the said o-aminophenols with phosgene can be used direct, i.e. without any need to isolate them first, in the novel preparation process.

The novel formazan dyes of the formula I can be obtained in a conventional manner. One possible option is to react a hydrazone of the formula VI

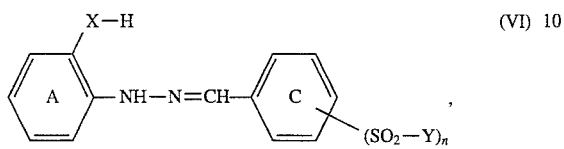

where n, X, Y and the rings A and C are each as defined above, with a diazonium salt derived from a formylaminophenol of the formula VII

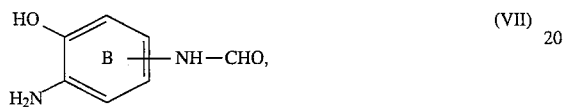

where the ring B is as defined above, in the presence of a copper or nickel salt, eg. copper sulfate or nickel sulfate, and then hydrolyzing the product by the method described in the earlier European Patent Application 93 107 173.0. The hydrazones of the formula VI are known from the earlier European Patent Application P 42 30 095.9. The preparation of the formylaminophenols VII is described in earlier European Patent Application 93 107 173.0.

The hydrolysis product is the dye of the formula VIII

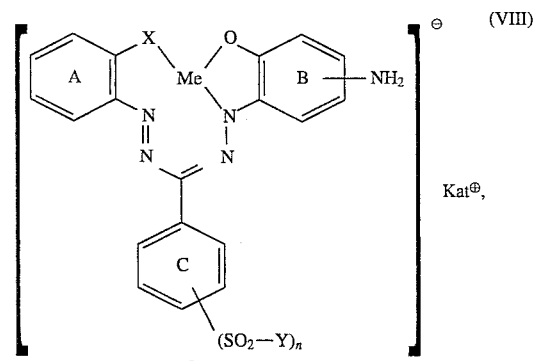

where n, Me, X, Y, Kat$^\oplus$ and the rings A, B and C are each as defined above, which can then be further reacted with a fiber-reactive component of the formula IX E—Lg    (IX)

where Lg is a leaving group, eg. chlorine or bromine, and E is as defined above.

In the preparation of those reactive dyes of the formula I which contain a triazine ring, the fiber-reactive component IX is for example cyanuric chloride. In this case the reaction with the dye of the formula VIII is followed by reaction with the amine of formula X

where $U^2$ and $U^3$ are each as defined above. It is also possible first to condense the cyanuric chloride with the amine X and then to react the resulting triazine derivative with the dye VIII.

However, it is also possible, in particular in the preparation of the formazan dyes of the formula Id, to employ the methods more particularly described in U.S. Pat. No. 5,023,274 or U.S. Pat. No. 4,841,028, both of which are hereby expressly incorporated herein by reference.

An advantageous method for preparing formazan dyes of the formula If further comprises reacting hydrazones of the formula VI with a diazonium salt derived from an aminophenol of the formula XI

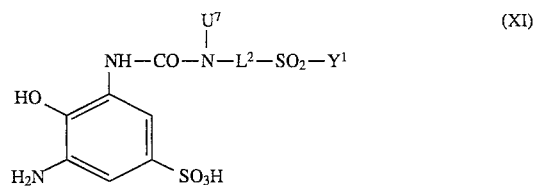

where $U^7$, $L^1$ and Y are each as defined above, in the presence of a copper or nickel salt, eg. copper sulfate or nickel sulfate.

The novel formazan dyes of the formula I are advantageously useful for dyeing or printing hydroxyl- or nitrogen-containing organic substrates. Examples of substrates of this type are leather and fiber materials predominantly comprising natural or synthetic polyamides or natural or regenerated cellulose. The novel dyes are particularly advantageous for dyeing and printing textile material based on wool or in particular cotton. The dyeings obtained have reddish blue shades.

Cellulose-based substrates in particular are dyed in deep shades with a very high degree of fixation, the dyeings having a very good lightfastness and excellent wetfastness properties, such as wash, chlorine bleach, peroxide bleach, alkali, seawater or perspiration fastness.

Embodiments of the invention will now be more particularly described by way of example.

EXAMPLE 1

34.8 g of 2-formylamino-6-aminophenol-4-sulfonic acid were dissolved in 300 ml of water, cooled down to 0° to 5° C. and adjusted to pH 2 with 50 ml of concentrated hydrochloric acid. Then the aminophenol was diazotized at 0°–5° C. with 40 g of 23% strength by weight aqueous sodium nitrite solution.

The resulting diazo suspension was added at 10°–15° C. to a pH 6.5–7.0 mixture of 53.6 g of the hydrazone of the formula

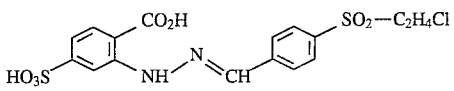

and 34.9 g of copper sulfate pentahydrate in 300 ml of water, the pH being maintained within the range from 6.5 to 7.0 by sprinkling with sodium bicarbonate. After the addition had ended, the mixture was stirred at 15°–20° C. for a further 12 hours.

It was then heated to 60° C., adjusted to pH 1 with concentrated hydrochloric acid and subsequently stirred at 60° C. for 3 hours.

Following complete hydrolysis (TLC) the pH was adjusted to 6.5 with sodium bicarbonate, and the precipitated product was filtered off and dried at 50° C. under reduced pressure.

The dried product obtained amounted to 95 g of an electrolyte-containing copper formazan of the formula
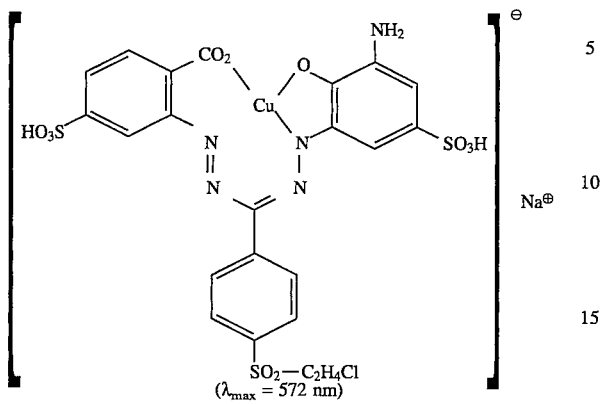
($\lambda_{max} = 572$ nm)
The same method gives the formazans listed below in Table 1.
TABLE 1
| Bsp.-Nr. | Kupferformazan |
|---|---|
| 2 | 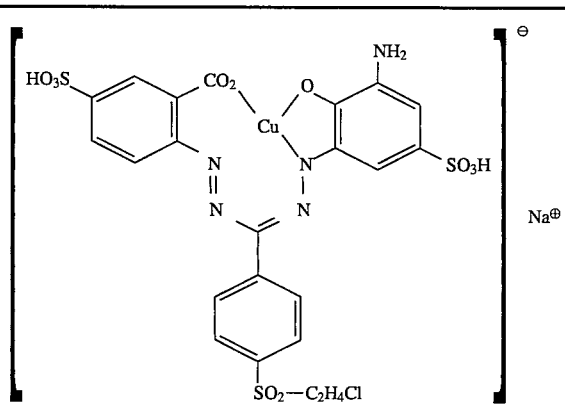 |
| 3 | 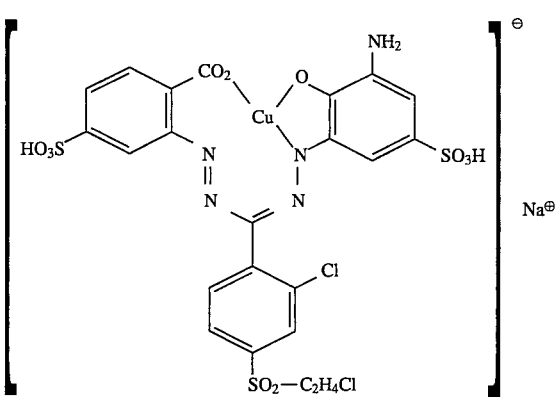 |

TABLE 1-continued
| Bsp.-Nr. | Kupferformazan |
|---|---|
| 4 | 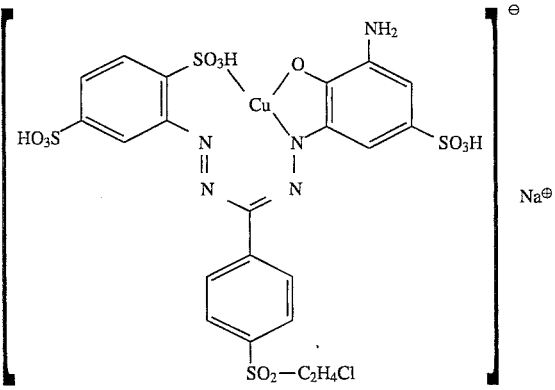 |
| 5 | 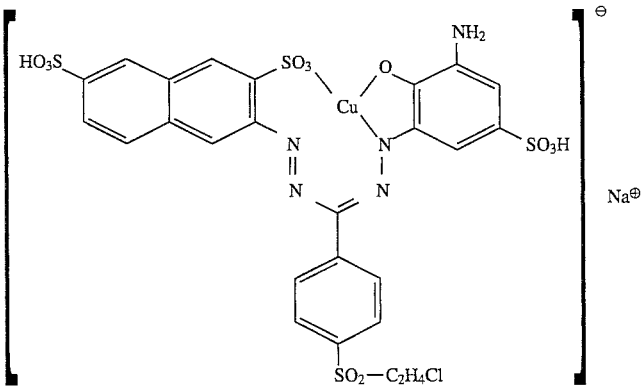 |
| 6 | 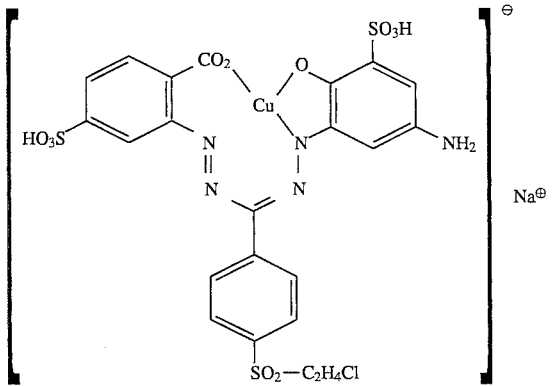 |
EXAMPLE 7
a) 19 g of the copper formazan compound of the formula

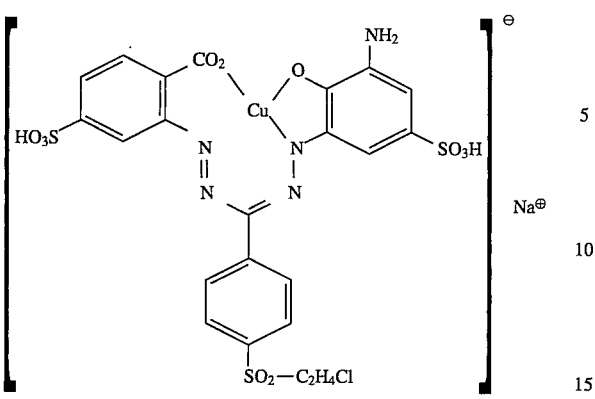

were dissolved in 200 ml of water. 0.6 g of disodium hydrogenphosphate was added, the mixture was cooled down to 0°–5° C. and a solution of 3.69 g of cyanuric chloride in 25 ml of acetone was added over 5 minutes. The pH was maintained at 6.0–6.5 with 5% strength by weight aqueous sodium bicarbonate solution, and the condensation was completed under the above conditions (TLC), which took about 1 hour.

b) Then a solution of 5 g of aniline-3-sulfonic acid in 200 ml of water, adjusted to pH 6, was added. The temperature was raised to 60° C and the mixture was subsequently stirred at that temperature for one hour while the pH was maintained at from 6.0 to 6.5 with 5% strength by weight aqueous sodium bicarbonate solution.

The resulting reactive dye was salted out with 150 g of sodium chloride. The dye obtained has the formula

EXAMPLE 8

Example 7 was repeated with 5.13 g of taurine instead of the aniline-3-sulfonic acid, affording, after salting out, a dye of the formula

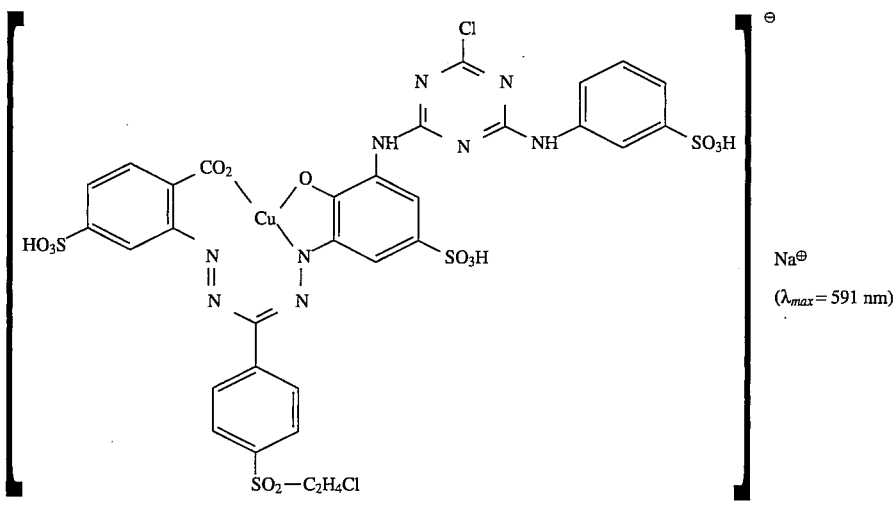

and dyes cotton in a reddish blue shade having very good fastness properties.

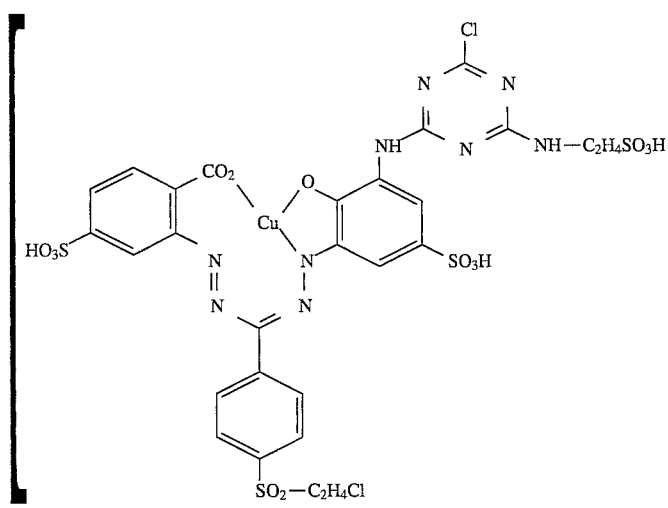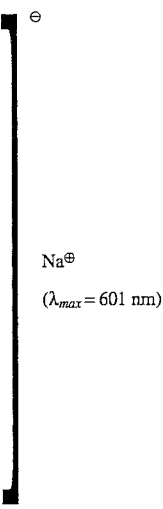

($\lambda_{max}$ = 601 nm)

which dyes cotton in a reddish blue shade with very good fastness properties.

EXAMPLE 9

9.33 g of 4-(2-sulfatoethyl)sulfonylaniline were dissolved in 200 ml of water at pH 6.5 and 0°–5° C. A suspension of 5.53 g of cyanuric chloride in 50 g of icewater was added and the mixture was subsequently stirred at 0°–5° C. and pH 6.5 for 2 hours.

The resulting suspension of the dichlorotriazine of the formula

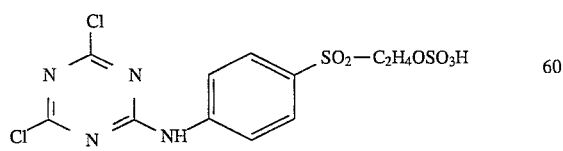

was admixed at 10°–15° C. with a solution in 150 ml of water of 15.7 g of the copper formazan described in Example 1.

The mixture was subsequently stirred at 10°–15° C. for 6 hours during which the pH was maintained at 6.0 to 6.5 with 5% strength by weight aqueous sodium bicarbonate solution.

The resulting reactive dye was salted out with 300 g of sodium chloride.

The dye obtained has the formula

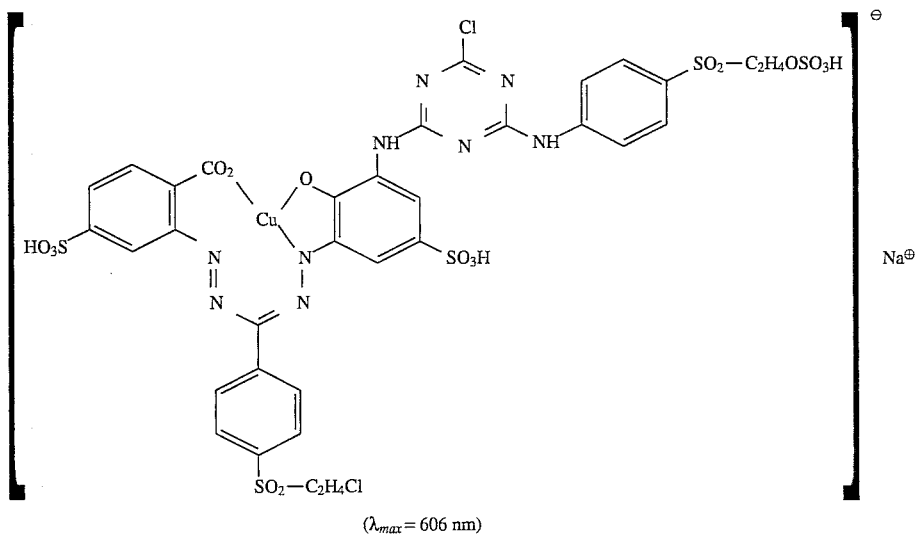

($\lambda_{max}$ = 606 nm)

and dyes cotton in a reddish blue shade having very good fastness properties.

The dyes listed below in Tables 2 and 3 can be obtained in a similar manner.

TABLE 2

[Structure: Copper complex dye with carboxylate, azo, and triazine substituents bearing X, Y groups; sulfonic acid at position 4 or 5; R substituent on middle ring; SO₂—C₂H₄Cl group; Na⁺ counterion]

| Bsp.-Nr. | Position von SO₃H | R | X | Y |
|---|---|---|---|---|
| 10 | 4 | H | Cl | HN—(C₆H₄)—SO₂—C₂H₄OSO₃H (meta) |
| 11 | 4 | H | Cl | N(C₂H₅)—(C₆H₄)—SO₂—C₂H₄OSO₃H (para) |
| 12 | 4 | H | Cl | N(C₂H₅)—C₆H₅ |
| 13 | 4 | H | Cl | HN—(C₆H₃)(SO₃H)₂ (2,5-disulfo) |
| 14 | 4 | H | Cl | HN—(C₆H₃)(CH₂SO₃H)(SO₂—C₂H₄Cl) |
| 15 | 4 | H | Cl | HN—(C₆H₄)—CO₂H (para) |
| 16 | 4 | H | Cl | HN—(C₆H₄)—NH—CO—NH—C₂H₄—SO₂—C₂H₄OSO₃H |

TABLE 2-continued
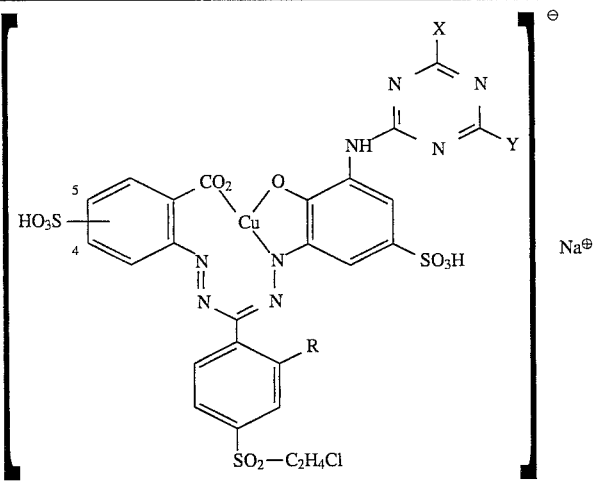
| Bsp.-Nr. | Position von SO₃H | R | X | Y |
|---|---|---|---|---|
| 17 | 4 | H | Cl | 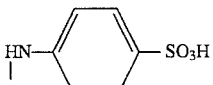 |
| 18 | 4 | H | Cl | 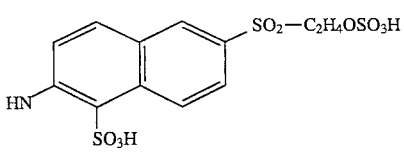 |
| 19 | 4 | H | Cl | 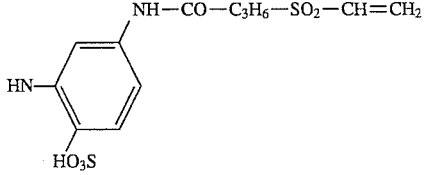 |
| 20 | 4 | H | Cl | 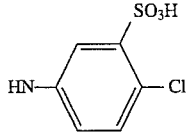 |
| 21 | 4 | H | Cl | 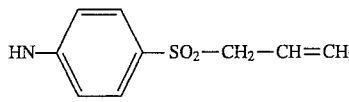 |
| 22 | 4 | H | Cl | NH₂ |
| 23 | 4 | H | Cl | NHCH₃ |
| 24 | 4 | H | Cl | NHCH₂CO₂H |
| 25 | 4 | H | Cl | N(CH₃)₂ |
| 26 | 4 | H | Cl |  |
| 27 | 4 | H | Cl | NH—C₂H₄OH |
| 28 | 4 | H | Cl | NH—C₂H₄—SO₂—C₂H₄Cl |
| 29 | 4 | H | Cl | NH—C₂H₄—SO₂—C₂H₄OSO₃H |
| 30 | 4 | H | Cl | 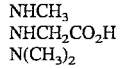 |

TABLE 2-continued
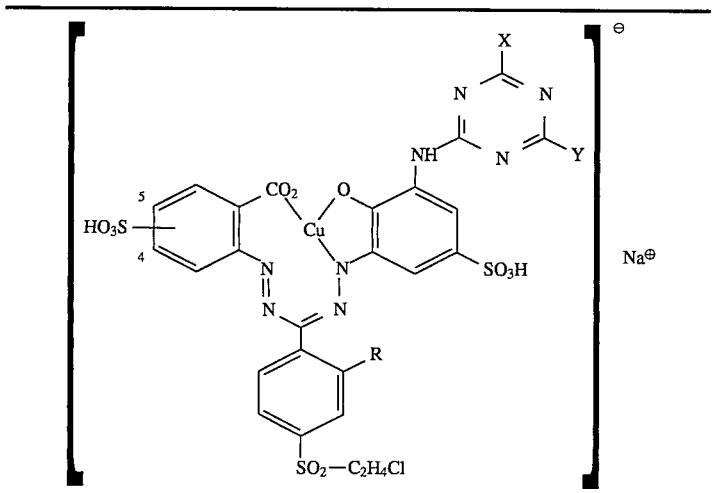
| Bsp.-Nr. | Position von SO₃H | R | X | Y |
|---|---|---|---|---|
| 31 | 4 | H | Cl | NH—C₂H₄OC₂H₄—SO₂—CH=CH₂ |
| 32 | 4 | H | Cl | N(CH₃)—C₂H₄—SO₂—C₂H₄Cl |
| 33 | 4 | H | Cl | NH—C₃H₆—SO₂—C₂H₄Cl |
| 34 | 4 | H | F | HN—C₆H₄(m)—SO₂—C₂H₄OSO₃H |
| 35 | 5 | H | Cl | N(Et)—C₆H₄(p)—SO₂—C₂H₄OSO₃H |
| 36 | 5 | H | Cl | N(C₂H₅)—C₆H₅ |
| 37 | 4 | Cl | Cl | HN—C₆H₃(2,5-(SO₃H)₂) |
| 38 | 4 | H | F | HN—C₆H₃(2-CH₂SO₃H, 4-SO₂—C₂H₄Cl) |
| 39 | 4 | Cl | Cl | HN—C₆H₄(p)—CO₂H |

TABLE 2-continued
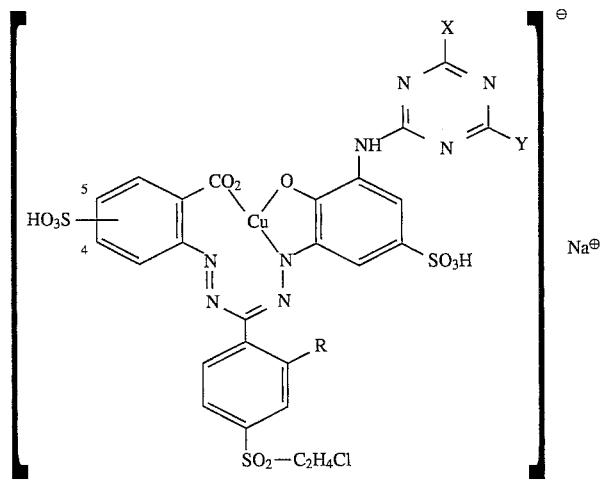
| Bsp.-Nr. | Position von SO₃H | R | X | Y |
|---|---|---|---|---|
| 40 | 4 | H | F | 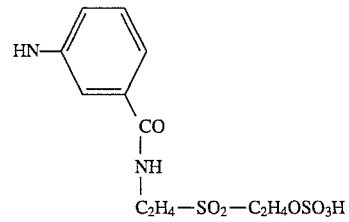 |
| 41 | 5 | H | F | 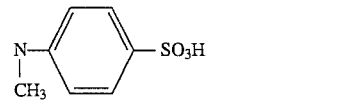 |
| 42 | 5 | H | Cl | 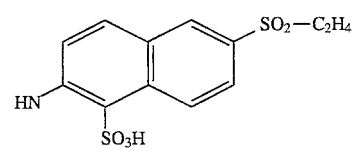 |
| 43 | 5 | H | F | 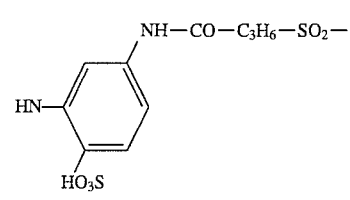 |
| 44 | 4 | Cl | Cl | 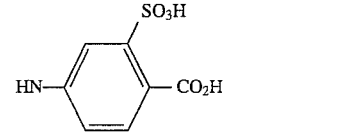 |
| 45 | 4 | H | F | 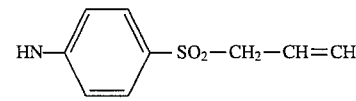 |
| 46 | 5 | H | Cl | NH₂ |
| 47 | 5 | Cl | Cl | NHCH₃ |
| 48 | 5 | H | Cl | NHCH₂CO₂H |
| 49 | 5 | Cl | Cl | N(CH₃)₂ |
| 50 | 4 | Cl | Cl |  |

TABLE 2-continued
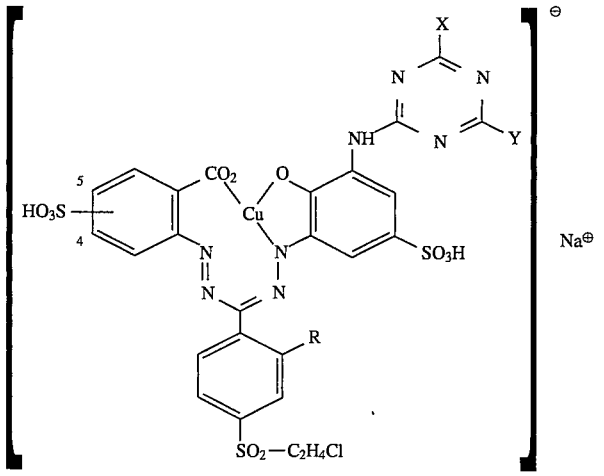
| Bsp.-Nr. | Position von SO₃H | R | X | Y |
|---|---|---|---|---|
| 51 | 4 | Cl | F | NH—C₂H₄OH |
| 52 | 4 | Cl | F | NH—C₂H₄—SO₂—C₂H₄Cl |
| 53 | 4 | H | F | NH—C₂H₄—SO₂—C₂H₄OSO₃H |
| 54 | 4 | H | F | N(C₂H₄—SO₂—C₂H₄Cl)₂ |
| 55 | 5 | H | F | NH—C₂H₄OC₂H₄—SO₂—CH=CH₂ |
| 56 | 5 | H | F | N(CH₃)—C₂H₄—SO₂—C₂H₄Cl |
| 57 | 5 | H | F | NH—C₃H₆—SO₂—C₂H₄Cl |
TABLE 3
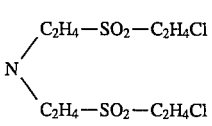
| Bsp.-Nr. | Position von SO₃H | X | Y |
|---|---|---|---|
| 58 | 4 | Cl | HN—C₆H₄—SO₂—C₂H₄OSO₃H |

TABLE 3-continued
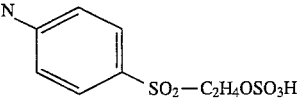
| Bsp.-Nr. | Position von SO₃H | X | Y |
|---|---|---|---|
| 59 | 5 | Cl | 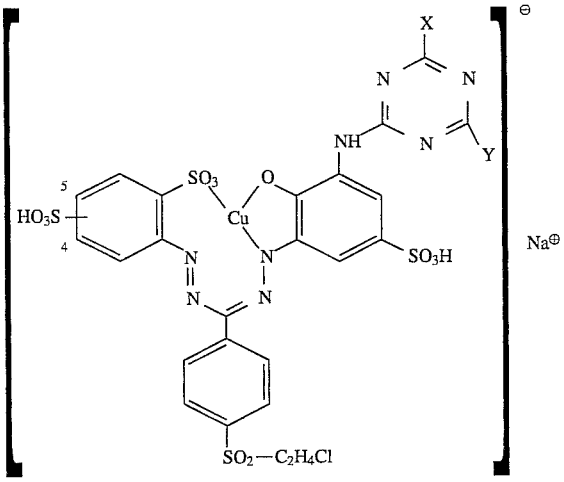 |
| 60 | 4 | F | 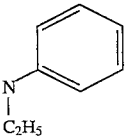 |
| 61 | 5 | Cl | 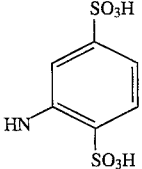 |
| 62 | 4 | Cl | HN—C₂H₄—SO₂—C₂H₄Cl |
| 63 | 4 | F | HN—C₂H₄OC₂H₄—SO₂—CH=CH₂ |
EXAMPLE 64
Example 7b was repeated with 15.9 g of the dichlorotriazinyl copper formazan described in Example 7a instead of the aniline-3-sulfonic acid, affording, after salting out, a reactive dye of the formula

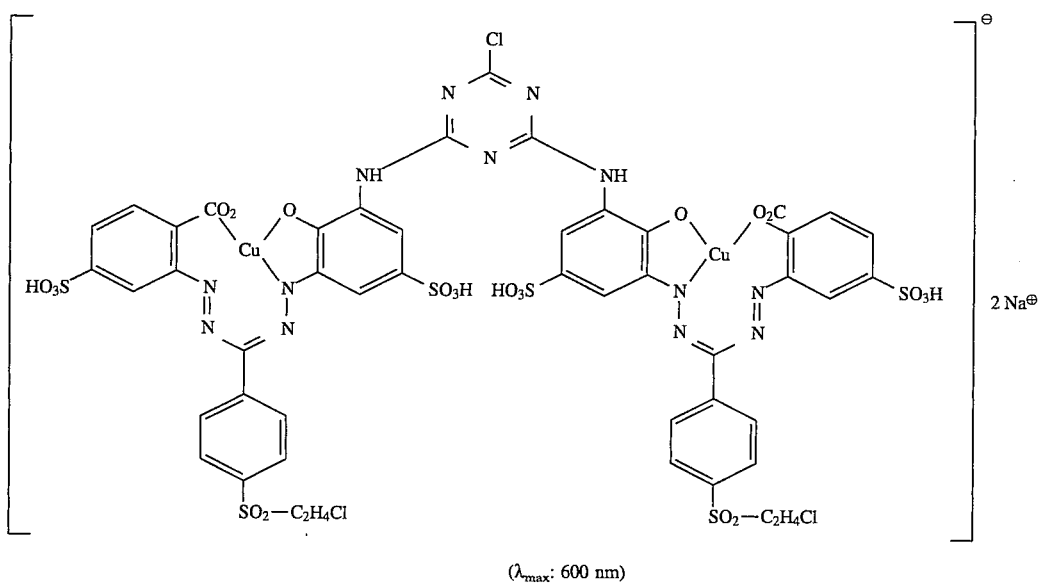

($\lambda_{max}$: 600 nm)

which dyes cotton in a deep reddish blue shade having very good fastness properties.

EXAMPLE 65

38 g of the dichlorotriazine of the formula

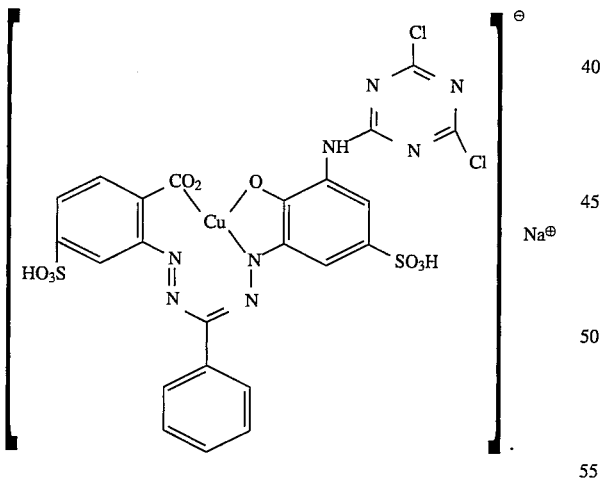

whose preparation is described in Example 1 of U.S. Pat. No. 5,004,807, were dissolved in 500 ml of water at pH 6.5 and 20°–25° C. After 20.9 g of the copper formazan dye of Example 1 had been added, the mixture was heated to 60° C. and subsequently stirred at that temperature for 3 hours during which the pH was maintained within the range from 6.0 to 6.5 with 5% strength by weight aqueous sodium bicarbonate solution. Cooling down to room temperature yielded the reactive dye of the formula

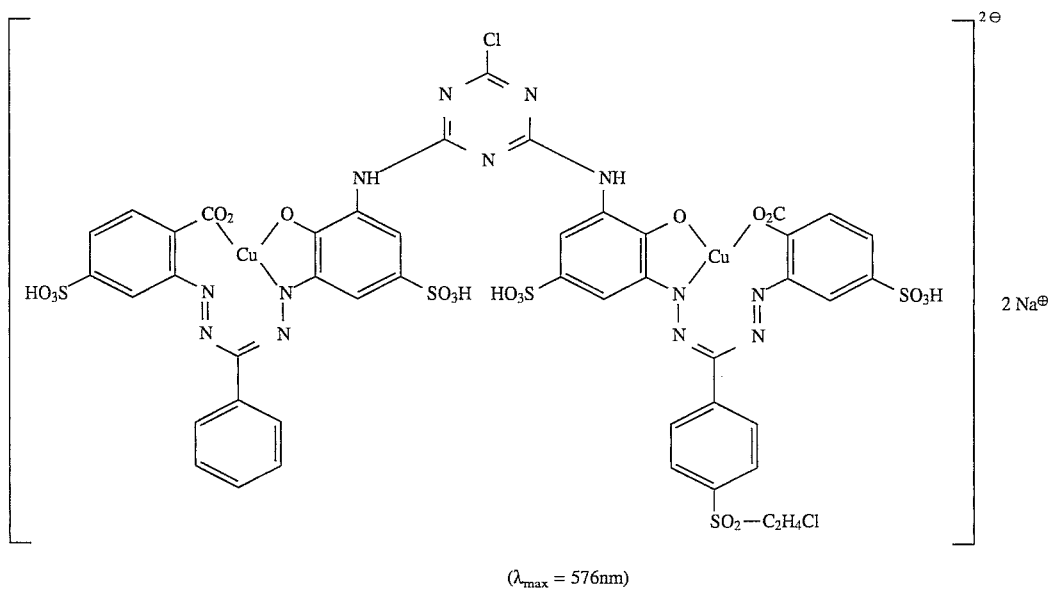

($\lambda_{max}$ = 576nm)

which dyes cotton in a reddish blue shade having very good fastness properties.

EXAMPLE 66

28.9 g of the copper formazan compound of the formula

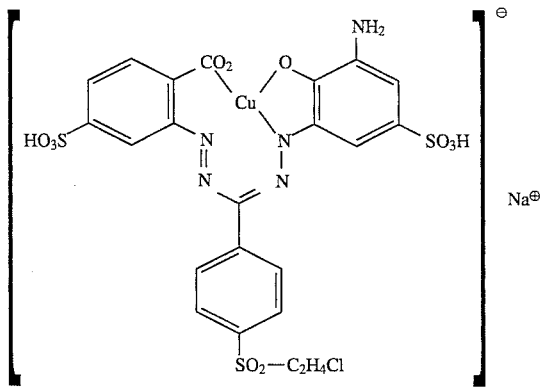

were dissolved in 400 ml of water. 0.6 g of disodium hydrogenphosphate was added, the mixture was cooled down to 0°–5° C., and a solution of 7.4 g of cyanuric chloride in 75 ml of acetone was added over 5 minutes. The pH was maintained within the range from 6.0 to 6.5 with 5% strength by weight aqueous sodium bicarbonate solution, and the condensation was completed under the above conditions (TLC), which took about 1 hour. Then a solution of 5.46 g of 2-methylamino-4-aminobenzenesulfonic acid in 100 ml of water, adjusted to pH 6, was added. The temperature was raised to 60° C. and the mixture was subsequently stirred at that temperature for 2 hours. Isolation by salting out with 150 g of sodium chloride yielded a dye of the formula

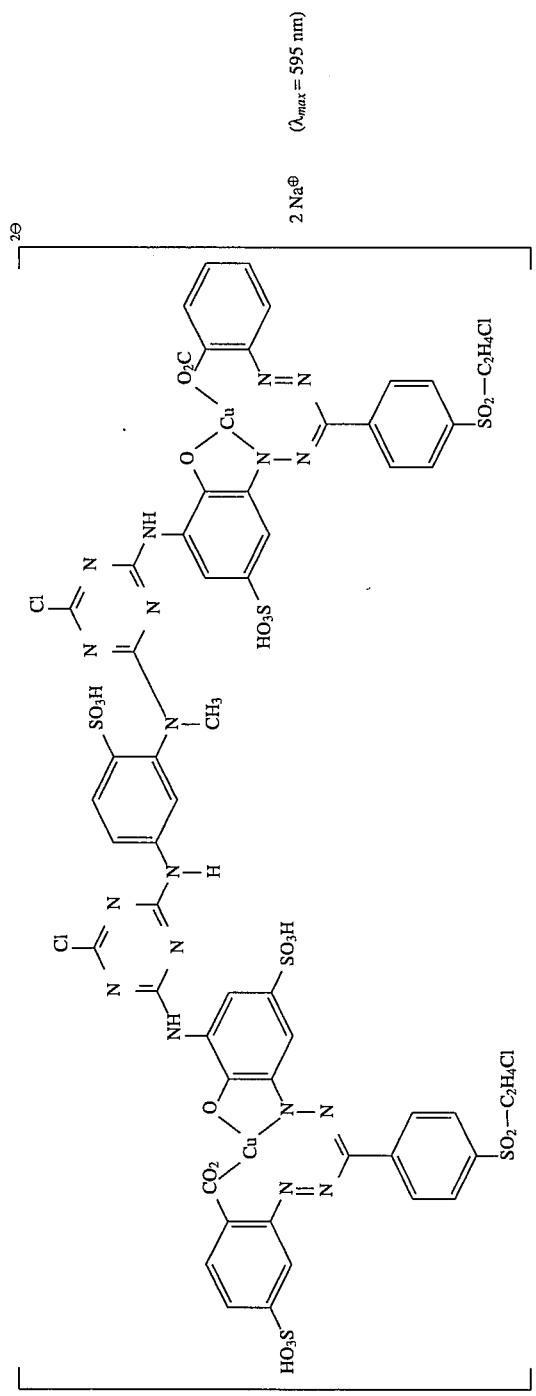

which dyes cotton in a reddish blue shade having very good fastness properties.

EXAMPLE 67

78.7 g of the aminophenol of the formula

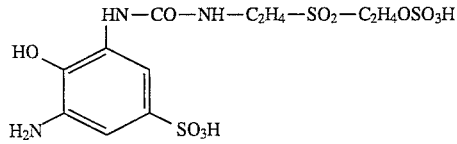

were dissolved in 600 ml of water, cooled down to 0°–5° C. and brought to pH 2 with concentrated hydrochloric acid. Then the aminophenol was diazotized at 0°–5° C. with 51 g of 23% strength by weight aqueous sodium nitrite solution.

The resulting diazo suspension was added at 10°–15° C. to a mixture, adjusted to pH 6.5–7.0, of 75.8 g of hydrazone of the formula

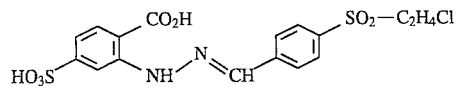

and 44.9 g of copper sulfate pentahydrate in 750 ml of water while the pH was maintained within the range from 6.5–7.0 by sprinkling with sodium bicarbonate. After the addition had ended, the mixture was stirred at 15°–20° C. for 12 hours.

The precipitated dye was filtered off with suction and washed with 20% strength by weight aqueous sodium chloride solution.

The moist filter residue obtained, which gives a bluish green solution in water and shows characteristic absorptions in the UV spectrum at 400 nm and 633 nm, was stirred up in 820 ml of water for the purpose of conversion into the more stable complex. The pH was adjusted to 1 with concentrated hydrochloric acid. The mixture was subsequently stirred at room temperature for 12 hours.

Sodium carbonate was added to adjust the pH to 6.5–7.0. The resulting reactive dye was salted out with 150 g of sodium chloride. The dye obtained has the formula

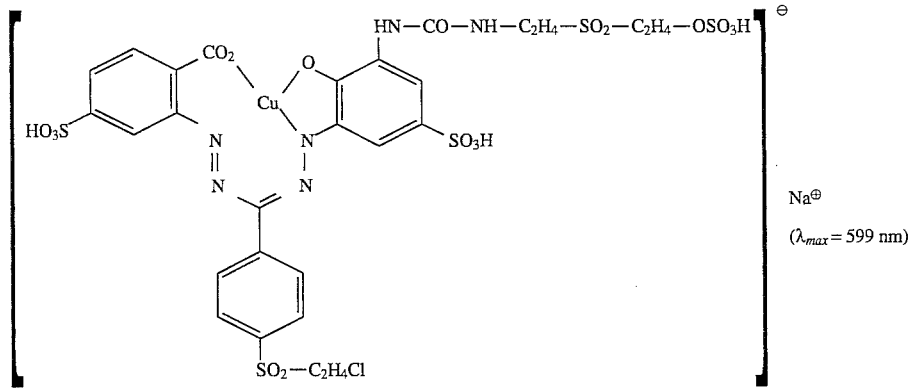

and dyes cotton in a deep reddish blue shade having very good fastness properties.

EXAMPLE 68

72.6 g of the copper formazan described in Example 1 were dissolved in 400 ml of water at pH 6 and cooled down to 0°–5° C. 26.5 g of the isocyanate of the formula

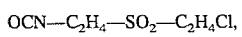

the preparation of which is described for example in Example 1 of U.S. Pat. No. 4,841,028, were added dropwise over 30 minutes during which the pH was maintained at from 6.0 to 6.2. After complete conversion (TLC), which took about 2 hours, the reactive dye formed was precipitated with 150 g of sodium chloride.

The dye obtained has the formula

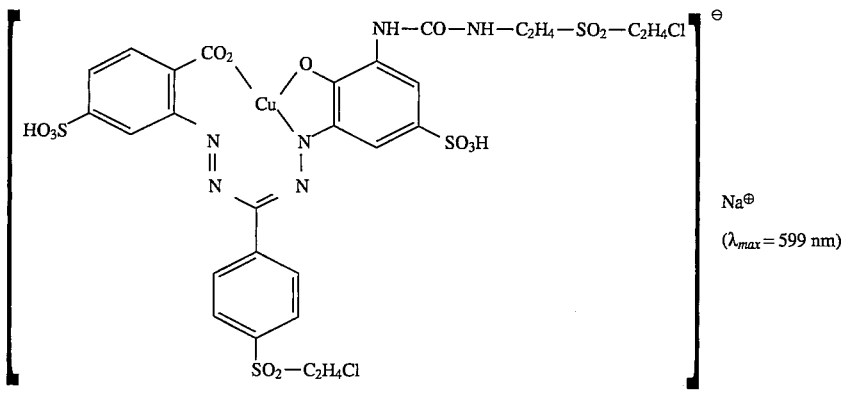

and dyes cotton in a deep reddish blue shade having very good fastness properties.

EXAMPLE 69

72.6 g of the copper formazan described in Example 1 were dissolved in 400 ml of water at pH 6.5 and cooled down to 5°–10° C. 26.8 g of the acid chloride of the formula

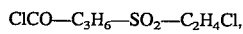

were added dropwise at pH 6.0–6.5 and 10° C. The mixture was subsequently stirred for 4 hours and then 100 g of sodium chloride were added. The precipitated dye was filtered off and dried at 40° C. under reduced pressure.

The reactive dye obtained has the formula

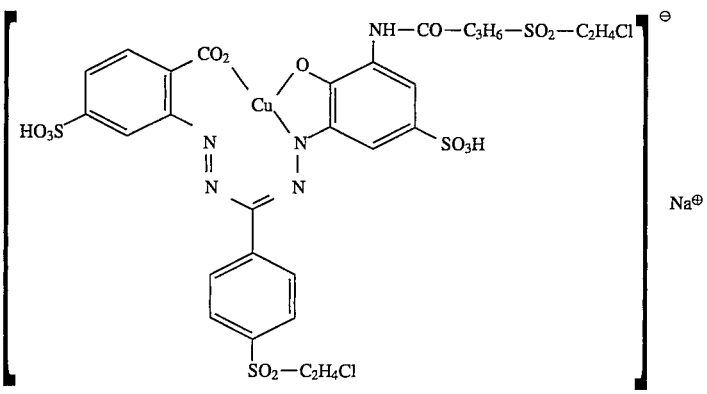

and dyes cotton in a deep reddish blue shade having very good fastness properties.

The method of Examples 67, 68 and 69 also gives the reactive dyes listed below in Table 4.

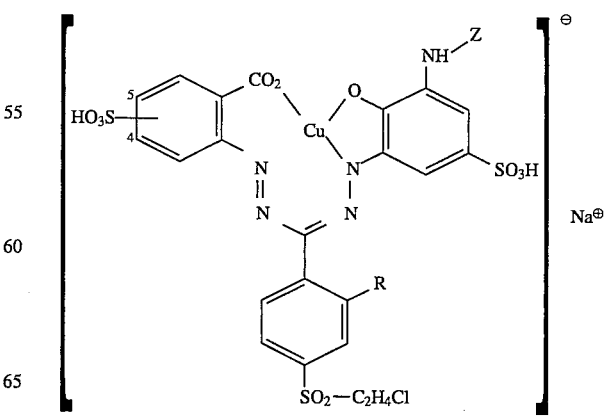

TABLE 4

| Ex. No. | Position of SO₃H | R | Z |
|---|---|---|---|
| 70 | 5 | H | CO—NH—C₂H₄—SO₂—C₂H₄OSO₃H |
| 71 | 4 | Cl | CO—NH—C₂H₄—SO₂—C₂H₄OSO₃H |
| 72 | 5 | H | CO—NH—C₂H₄—SO₂—C₂H₄Cl |
| 73 | 4 | H | CO—NH—C₂H₄—SO₂—C₂H₄OCOCH₃ |
| 74 | 5 | H | CO—NH—C₂H₄—SO₂—C₂H₄OCOCH₃ |
| 75 | 4 | H | CO—NH—C₃H₆—SO₂—C₂H₄OSO₃H |
| 76 | 4 | Cl | CO—NH—C₃H₆—SO₂—C₂H₄OSO₃H |
| 77 | 5 | H | CO—NH—C₃H₆—SO₂—C₂H₄OSO₃H |
| 78 | 4 | H | CO—NCH₃—C₂H₄—SO₂—C₂H₄OSO₃H |
| 79 | 5 | H | CO—NCH₃—C₂H₄—SO₂—C₂H₄OSO₃H |
| 80 | 4 | H | CO—NCH₃—C₂H₄—SO₂—C₂H₄Cl |
| 81 | 4 | H | CO—N(C₂H₄—SO₂—C₂H₄OSO₃H)₂ |
| 82 | 5 | H | CO—N(C₂H₄—SO₂—C₂H₄OSO₃H)₂ |
| 83 | 4 | Cl | CO—N(C₂H₄—SO₂—C₂H₄OSO₃H)₂ |
| 84 | 4 | H | CO—NH—C₂H₄O—C₂H₄—SO₂—C₂H₄OSO₃H |
| 85 | 5 | H | CO—NH—C₂H₄O—C₂H₄—SO₂—C₂H₄OSO₃H |
| 86 | 4 | Cl | CO—NH—C₂H₄O—C₂H₄—SO₂—C₂H₄OSO₃H |
| 87 | 4 | H | CO—N(C₂H₄—SO₂—C₂H₄Cl)₂ |
| 88 | 5 | H | CO—N(C₂H₄—SO₂—C₂H₄Cl)₂ |
| 89 | 4 | H | 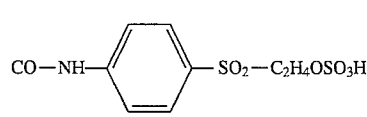 |
| 90 | 4 | H | 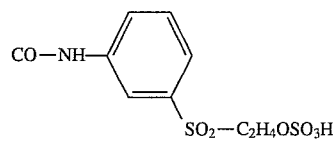 |
| 91 | 4 | H | 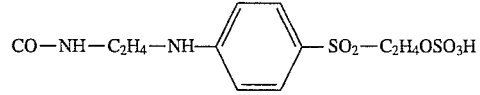 |
| 92 | 5 | H | CO—C₃H₆—SO₂—C₂H₄Cl |
| 93 | 4 | Cl | CO—C₃H₆—SO₂—C₂H₄Cl |
| 94 | 4 | H | 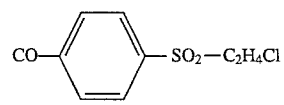 |
| 95 | 5 | H | 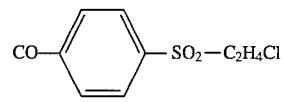 |
| 96 | 4 | H | 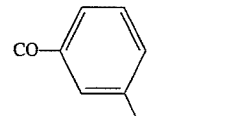 |
| 97 | 4 | Cl | 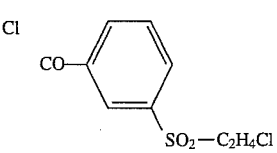 |
| 98 | 4 | H | 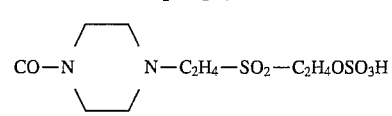 |
| 99 | 5 | H | 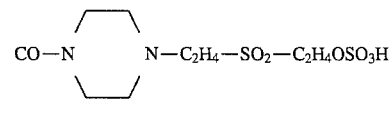 |

TABLE 4-continued

| Ex. No. | Position of SO₃H | R | Z |
|---|---|---|---|
| 100 | 4 | H | CO—NH—C₂H₄—⟨phenyl⟩—SO₂—C₂H₄OSO₃H |
| 101 | 5 | H | CO—NH—C₂H₄—⟨phenyl⟩—SO₂—C₂H₄OSO₃H |
| 102 | 4 | H | CO—NH—C₂H₄—⟨phenyl⟩—SO₂—C₂H₄Cl |

EXAMPLE 103 a) To 160 g of sodium hydroxide in 1.5 l of water 232 g of 3-amino-4-hydroxy-5-nitrobenzenesulfonic acid were added with cooling at 20°–40° C. The reaction mixture was cooled down to 0°–5° C., and then 182 g of phosgene were introduced over 8 hours while the pH was maintained at ≦10 with 150 g of 50% strength by weight sodium hydroxide solution. The mixture was subsequently stirred for one hour, and excess phosgene was then expelled with nitrogen. The pH was adjusted to 7 with 200 g of concentrated hydrochloric acid. To the resulting 7-nitrobenzoxazol-2-one- 5-sulfonic acid (sodium salt) were added 133 g of 2'-aminoethyl 2-hydroxyethyl sulfide and the pH was adjusted to 7 with 164 g of concentrated hydrochloric acid. The mixture was heated to 60° C. and stirred at that temperature for 6.5 hours. After complete conversion (TLC), it was adjusted to pH 5 with concentrated hydrochloric acid, and 0.50 g of tungstic acid were added, followed over 2 hours by the dropwise addition of 340 g of 30% strength by weight hydrogen peroxide. The mixture was subsequently stirred at 60° C. for a further 2 hours until conversion was complete (TLC). After cooling down to 0°–5° C. the mixture was adjusted to pH 0.5–1.0 with 150 g of concentrated hydrochloric acid, and the precipitated product was filtered off with suction. Drying at 70°–80° C. under reduced pressure yielded 377 g of a compound of the formula

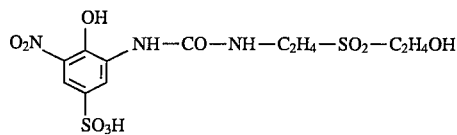

$^1$H-NMR [D$^6$-DMSO]: δ=3.3 (CH₂), 3.4 (CH₂), 3.6 (CH₂), 3.8 (CH₂), 5.2 (OH), 7.3 (NH), 7.7, 8.6 (aromatics H), 11.0 (NH) ppm b) 306 g of the nitro compound obtained under a) were dissolved in 3 l of water. 5 g of palladium catalyst (10% strength on carbon) were added, and a hydrogenation was carried out at 35°–40° C. After the uptake of hydrogen had ceased, the catalyst was filtered off and the mother liquor was evaporated to dryness, leaving 280 g of the compound of the formula

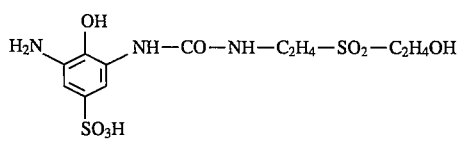

$^1$H-NMR [D$^6$-DMSO]: δ=3.30, 3.35, 3.55, 3.80 (in each case CH₂), 4.00 (OH), 7.10 (NH), 7.35, 7.50 (aromatics H), 9.20 (OH) 11.5 (NH)

EXAMPLE 104

280 g of the aminophenol obtained in Example 103b were added with ice-cooling at 10°–15° C. to 1120 g of chlorosulfonic acid and the mixture was subsequently stirred at room temperature for about 12 hours. After conversion was complete (TLC), the mixture was poured onto 4 l of ice, and the precipitated product was filtered off with suction and washed neutral with water. Drying under reduced pressure at 30°–40° C. left 302 g of the compound of the formula

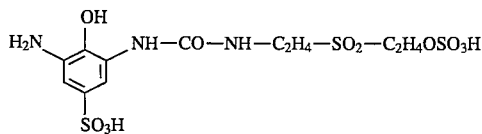

which can be used without further purification for dye syntheses as described for example in Example 67.

EXAMPLE 105 a) Example 103a was repeated, except that the 3-amino-4-hydroxy-5-nitrobenzenesulfonic acid was replaced by 232 g of the isomeric 2-hydroxy-3-amino-5-nitrobenzenesulfonic acid affording, after drying at 70°–80° C. under reduced pressure, 365 g of a compound of the formula

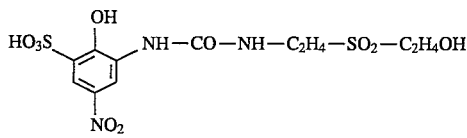

b) The nitro compound described under a) was reduced according to Example 103b and 280 g of the resulting amino compound were esterified with chlorosulfonic acid according to Example 104, affording, after drying at 30°–40° C. 295 g of the compound of the formula

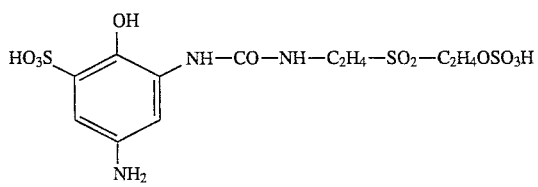

The method of Example 103 or 104 also gives the aminophenols listed below in Table 5.

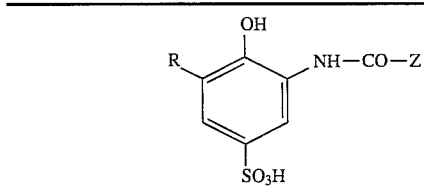

| Example No. | R | Z |
|---|---|---|
| 106 | $NO_2$ | $NHC_3H_6SO_2C_2H_4OH$ |
| 107 | $NH_2$ | $NHC_3H_6SO_2C_2H_4OH$ |
| 108 | $NH_2$ | $NHC_3H_6SO_2C_2H_4OSO_3H$ |
| 109 | $NO_2$ | $N(CH_3)C_2H_4SO_2C_2H_4OH$ |
| 110 | $NH_2$ | $N(CH_3)C_2H_4SO_2C_2H_4OH$ |
| 111 | $NH_2$ | $N(CH_3)C_2H_4SO_2C_2H_4OSO_3H$ |
| 112 | $NO_2$ | $NHC_2H_4OC_2H_4SO_2C_2H_4OH$ |
| 113 | $NH_2$ | $NHC_2H_4OC_2H_4SO_2C_2H_4OH$ |
| 114 | $NH_2$ | $NHC_2H_4OC_2H_4SO_2C_2H_4OSO_3H$ |
| 115 | $NO_2$ | N⌒N—$C_2H_4SO_2C_2H_4OH$ |
| 116 | $NH_2$ | N⌒N—$C_2H_4SO_2C_2H_4OH$ |
| 117 | $NH_2$ | N⌒N—$C_2H_4SO_2C_2H_4OSO_3H$ |
| 118 | $NO_2$ | $N(C_2H_4SO_2C_2H_4OH)_2$ |
| 119 | $NH_2$ | $N(C_2H_4SO_2C_2H_4OH)_2$ |
| 120 | $NH_2$ | $N(C_2H_4SO_2C_2H_4OSO_3H)_2$ |
| 121 | $NO_2$ | $HNC_2H_4NH$—⌬—$SO_2C_2H_4OH$ |
| 122 | $NH_2$ | $HNC_2H_4NH$—⌬—$SO_2C_2H_4OH$ |
| 123 | $NH_2$ | $HNC_2H_4NH$—⌬—$SO_2C_2H_4OSO_3H$ |

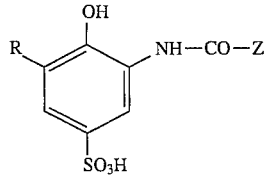

| Example No. | R | Z |
|---|---|---|
| 124 | $NO_2$ | $HNC_2H_4$—⌬—$SO_2C_2H_4OH$ |
| 125 | $NH_2$ | $HNC_2H_4$—⌬—$SO_2C_2H_4OH$ |
| 126 | $NH_2$ | $HNC_2H_4$—⌬—$SO_2C_2H_4OSO_3H$ |

We claim:

1. An Aminophenol of the formula II

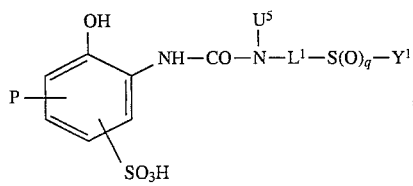

where q is 0 or 2, $Y^1$ is vinyl or a radical of the formula $C_2H_4$—$Q^1$, wherein $Q^1$ is a group that is detachable under alkaline reaction conditions or hydroxyl, $L^1$ is $C_2$–$C_6$-alkylene, which may be substituted by hydroxyl, chlorine, cyano, carboxyl, $C_1$–$C_4$-alkoxycarbonyl, $C_1$–$C_4$-alkanoyloxy or sulfato and may be interrupted by 1 or 2 oxygen atoms in ether function or by imino or $C_1$–$C_4$-alkylimino groups, $U^5$ is hydrogen or $C_1$–$C_6$-alkyl, which may be substituted by hydroxyl, $C_1$–$C_4$-alkoxy, halogen, cyano, hydroxysulfonyl or a radical of the formula —$SO_2$—$Y^1$, wherein $Y^1$ is as defined above, or is substituted or unsubstituted phenyl, and P is nitro or amino.

* * * * *